US 6,727,371 B2

(12) United States Patent
Müller et al.

(10) Patent No.: US 6,727,371 B2
(45) Date of Patent: Apr. 27, 2004

(54) METHOD FOR CONVERTING AN ORGANIC COMPOUND WITH A HYDROPEROXIDE

(75) Inventors: Ulrich Müller, Neustadt (DE); Joaquim Henrique Teles, Otterstadt (DE); Norbert Rieber, Mannheim (DE); Andreas Walch, Schwaigern (DE); Peter Bassler, Viernheim (DE); Alwin Rehfinger, Mutterstadt (DE); Anne Wenzel, Eggenstein-Leopoldshafen (DE); Wolfgang Harder, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 130 days.

(21) Appl. No.: 10/240,278
(22) PCT Filed: Mar. 19, 2001
(86) PCT No.: PCT/EP01/03143
§ 371 (c)(1),
(2), (4) Date: Sep. 30, 2002
(87) PCT Pub. No.: WO01/72729
PCT Pub. Date: Oct. 4, 2001

(65) Prior Publication Data
US 2003/0050487 A1 Mar. 13, 2003

(30) Foreign Application Priority Data
Mar. 28, 2000 (DE) .......................... 100 15 246

(51) Int. Cl.$^7$ ............................................. C07D 301/12
(52) U.S. Cl. ........................................................ 549/531
(58) Field of Search ......................................... 549/531

(56) References Cited

U.S. PATENT DOCUMENTS

| | | | | |
|---|---|---|---|---|
| 2,338,881 A | * | 1/1944 | Thomas | |
| 3,329,603 A | * | 7/1967 | Hughes et al. | |
| 3,346,658 A | * | 10/1967 | Mulaskey et al. | |
| 3,591,629 A | * | 7/1971 | Stancell et al. | |
| 4,883,260 A | * | 11/1989 | Kanda | |
| 4,973,778 A | * | 11/1990 | Hartley et al. | |
| 5,059,738 A | * | 10/1991 | Beech, Jr. et al. | |
| 5,262,550 A | * | 11/1993 | Crocco et al. | |
| 5,349,072 A | * | 9/1994 | Preston et al. | |
| 5,489,726 A | * | 2/1996 | Wood et al. | |
| 5,849,937 A | * | 12/1998 | Jubin, Jr. et al. | |
| 5,912,367 A | * | 6/1999 | Chang | |

* cited by examiner

*Primary Examiner*—Taofiq A. Solola
(74) *Attorney, Agent, or Firm*—Oblon, Spivak, McClelland, Maier & Neustadt, P.C.

(57) ABSTRACT

In a continuous process for reacting an organic compound with hydroperoxide in the presence of a catalyst, the reaction is carried out in a reactor assembly comprising at least two reactors connected in parallel.

12 Claims, No Drawings

METHOD FOR CONVERTING AN ORGANIC COMPOUND WITH A HYDROPEROXIDE

This application is a 371 of PCT/EP01/03143 filed Mar. 19, 2001.

FIELD OF INVENTION

The present invention relates to a process for reacting an organic compound with a hydroperoxide using at least two reactors connected in parallel. The invention further provides the apparatus itself in which the process is carried out, and quite generally provides for the use of this apparatus for carrying out the process.

BACKGROUND INFORMATION

Reactions of organic compounds with hydroperoxides, i.e. compounds of the formula ROOH, are generally carried out in a single stage in customary processes of the prior art.

For example, U.S. Pat. No. 5,262,550 describes a process for the epoxidation of alkenes in which alkene is reacted in one step with hydrogen peroxide or a hydrogen peroxide precursor to give the corresponding alkene oxide.

U.S. Pat. No. 4,883,260 discloses a process in which alkene is reacted with hydrogen peroxide in one step in a steel autoclave or in a glass autoclave.

S. H. Wang, Process Economics Program, Report 2E, p. 6–1 to 6–27, SRI International (1994), for example, describes a process in which an about 17% strength by weight solution of ethylbenzene hydroperoxide is reacted with propene in a single step over a homogeneous Mo catalyst.

The same document discloses, on pages 6–28 to 6–47, a process in which an about 20% strength by weight solution of ethylbenzene hydroperoxide is reacted with propene in a single step over a heterogeneous $Ti/SiO_2$ catalyst, with the alkene being epoxidized.

This document likewise discloses, on pages 51 to 521, a process in which an about 40% strength by weight solution of tert-butyl hydroperoxide is reacted with propene in a single step over a homogeneous Mo catalyst, with the alkene being epoxidized.

Two-stage processes are also known from the prior art.

For example, the abovementioned SRI publication discloses, on pages 522 to 543, a process in which an about 72% strength by weight solution of tert-butyl hydroperoxide is reacted with propene over a homogeneous Mo catalyst in two directly successive stages, with the alkene being epoxidized.

U.S. Pat. No. 5,849,937 describes a process for the epoxidation of an olefin using a cascade of at least two fixed-bed reactors connected in series.

BRIEF SUMMARY

It is an object of the present invention to provide a process which allows a high throughput of feed streams and is, in particular, configured so that regeneration of catalysts used in the reaction of the organic compound with hydroperoxide can also be carried out in a simple way.

DETAILED DESCRIPTION OF THE INVENTION

We have found that this object is achieved by a continuous process for reacting an organic compound with hydroperoxide in the presence of a catalyst, wherein the reaction is carried out in a reactor assembly comprising at least two reactors connected in parallel.

Both single-stage and also two-stage and multistage processes are conceivable for carrying out the reaction. If multistage process configurations are chosen, it has to be ensured that at least one of the stages has at least one reactor assembly comprising at least two reactors connected in parallel.

For example, it is conceivable for the process to have a reaction stage (R1) in which the organic compound is reacted in the presence of a catalyst to give a product stream (P1), with a reactor assembly comprising two or more reactors connected in parallel being selected for reaction stage (R1). Likewise, (R1) can have a reactor assembly comprising at least two reactor cascades connected in parallel, with each reactor cascade having at least two reactors connected in series. It is also conceivable to have reactor assemblies in which at least one such reactor cascade is connected in parallel to at least one further reactor.

Apart from the reaction stage or stages, the process of the present invention can further comprise at least one intermediate treatment in which at least one product stream resulting from at least one reaction stage is treated in an appropriate manner.

For example, it is conceivable for the process to have a reaction stage (R1) as described above in which the organic compound is reacted in the presence of a catalyst to give a product stream (P1) and the product stream is passed to an intermediate treatment (I1). The product stream (PI1) resulting from the intermediate treatment (I1) can, for example, be recirculated to the reaction stage (R1) in order, for example, to react unreacted organic compound or/and unreacted hydroperoxide. Likewise, the product stream (PI1) can be fed to a further reaction stage (R2). It is also possible, for example, for the product stream (PI1) to be divided in an appropriate manner into at least two substreams and at least one of the substreams to be recirculated to (R1) and at least one of the substreams to be passed to the reaction stage (R2).

In principle, any desired reaction which can be carried out using the product stream (PI1) or the substream or substreams of (PI1) can be performed in (R2). In the process of the present invention, preference is given to feeding the product stream (PI1) comprising hydroperoxide to the reaction stage (R2) and reacting hydroperoxide with the organic compound in the presence of a catalyst in (R2) to give a product stream (P2).

The present invention accordingly provides a continuous process, as described above, for reacting an organic compound with hydroperoxide, in which the organic compound is reacted with hydroperoxide in the presence of a catalyst in a reaction stage (R1) to give at least one product stream (P1), the product stream or streams (P1) is passed to an intermediate treatment (I1) to give, as output from (I1), at least one product stream (PI1) comprising hydroperoxide, and the product stream or streams (PI1) is passed to a reaction stage (R2) in which hydroperoxide is reacted with the organic compound in the presence of a catalyst to give at least one product stream (P2), wherein at least two reactors connected in parallel are used in at least one of the reaction stages (R1) and (R2).

The present invention thus encompasses embodiments in which, for example, two or more reactors connected in parallel are used in the reaction stage (R1) and one reactor is used in the reaction stage (R2). It likewise encompasses embodiments in which one reactor is used in reaction stage (R1) and two or more reactors connected in parallel are used in reaction stage (R2). Furthermore, it also encompasses embodiments in which two or more reactors connected in parallel are used in reaction stage (R1) and two or more reactors connected in parallel are used in stage (R2), where the number of parallel reactors used in stage (R1) can be identical to or different from the number of parallel reactors used in stage (R2).

The number of feed streams which are introduced into the reactor or reactors in (R1) can essentially be chosen without restriction. All starting materials can, for example, be introduced as individual streams into the reactor or reactors. Likewise, the feed streams can be combined in an appropriate manner before introduction into the reactor or reactors and the resulting stream or streams can be introduced into the reactor or reactors. For example, it is conceivable for a reactor of (R1) to be fed with a feed stream which already has the composition of the mixture which is reacted in the reactor.

Quite generally, the feed stream or streams can be pretreated before it is introduced into a reactor of stage (R1). All methods are conceivable for this pretreatment. For example, at least one basic compound, at least one neutral compound, at least one acidic compound or a mixture of two or more of these compounds can be added to one or more feed streams used in (R1), with preference being given to adding a basic compound as is discussed below in respect of the intermediate treatment (I1).

Depending on the number of reactors used in stage (R1), stage (R1) results in a differing number of product streams which are passed to the intermediate treatment (I1). For example, it is conceivable for a product stream from (R1) to be divided in an appropriate manner into a plurality of streams and be fed to a plurality of apparatuses in which the intermediate treatment (I1) is carried out. Likewise, a plurality of product streams from (R1) can be combined to form one or more streams and fed to one or more apparatuses in which the intermediate treatment (I1) is carried out.

As regards the intermediate treatment (I1), it is possible, quite generally, to employ all conceivable combinations of identical or different apparatuses connected in series and/or in parallel.

For the purposes of the present invention, the term "intermediate treatment" refers to all treatments which have an appropriate influence on the chemical or physical properties of the product stream from the reaction stage (R1), with, in contrast to the reaction stages (R1) and (R2), the reaction of organic compound with hydroperoxide being able to occur but playing only a subordinate role. Accordingly, a conceivable intermediate treatment is, for example, addition of one or more compounds to a product stream, separation of one or more compounds from a product stream or, for instance, altering the temperature or altering the pressure or altering the physical state of a product stream or altering the physical state of at least one chemical compound present in a product stream. Further conceivable intermediate treatments are, for example, mixing processes by means of which, for example, the homogeneity of a product stream can be influenced.

If the intermediate treatment is carried out, for example, in an apparatus provided specifically for the intermediate treatment; for example in a reactor, a separation apparatus, a mixing apparatus or the like, the number of these apparatuses is in principle independent of the number of reactors used in stage (R1) and the number of reactors used in stage (R2).

Thus, for example, if two or more reactors connected in parallel are used in stage (R1), the product streams from these reactors can be combined in a suitable manner to form a single stream and this single stream can be passed to the intermediate treatment in a single apparatus. It is likewise conceivable for two or more product streams not to be combined or to be combined in an appropriate manner to form two or more streams and each of these streams to be passed to intermediate treatment in a separate apparatus. It is also possible for the product stream which results from (R1) if only one reactor is used in stage (R1) to be passed to intermediate treatment in a single apparatus or for this single product stream to be divided into two or more streams and each of the resulting streams to be fed to a single or, in an appropriate manner, to two or more apparatuses in which the intermediate treatment is carried out.

The present invention also encompasses embodiments in which the intermediate treatment (I1) is carried out in at least two apparatuses which are connected in series, in which case the apparatuses can be identical or different. It likewise encompasses embodiments in which at least one product stream (P1) is, in (I1), subjected to intermediate treatment in one or more apparatuses connected in parallel and at least one further product stream (P1) is subjected to intermediate treatment as described for (I1) in at least one apparatus cascade. It also encompasses embodiments in which at least two product streams are each separately subjected to intermediate treatment in a suitable apparatus in a first step of the intermediate treatment (I1) and the streams resulting from this step in the first apparatus are combined in an appropriate manner in at least one further apparatus which may be identical to or different from the first apparatus and subjected to intermediate treatment in a further step of (I1).

Regardless of the number of apparatuses in which the intermediate treatment (I1) is carried out, the reaction stage (R2) can be carried out in one reactor or in two or more reactors connected in parallel. However, if only one reactor is used in (R1), at least two reactors connected in parallel are used in (R2).

In this regard, it is conceivable for each reactor of stage (R2) to be fed with one or more feed streams resulting as product streams (PI1) from the intermediate treatment (I1), with a stream resulting as product stream from the intermediate treatment (I1) being able to be combined in an appropriate manner with at least one further product stream (PI1), or a stream (PI1) being able to be divided into at least two streams.

The present invention thus encompasses, inter alia, an embodiment in which, for example, at least one compound, for example a basic compound, is added to each of x (x>1) feed streams comprising at least hydroperoxide, organic compound and solvent, the resulting steams are each fed to a reactor of reaction stage (R1), where (R1) thus has x reactors connected in parallel, the product stream (P1) from each of the reactors of (R1) is subjected to an intermediate treatment (I1), where, for example, at least one compound which may be identical to or different from the compound added to the feed streams is again added separately to each product stream from (R1) and each of the resulting x streams (PI1) are each introduced into a reactor of the reaction stage (R2) which thus has x reactors connected in parallel.

The present invention likewise encompasses, for example, an embodiment in which at least one compound, for example a basic compound, is added to each of x feed streams comprising at least hydroperoxide, organic compound and solvent, the resulting streams are each fed to a reactor of the reaction stage (R1), where (R1) thus has x reactors connected in parallel, the product streams (P1) are combined to form a single stream and the resulting stream is passed to an intermediate treatment (I1) and the stream (PI1) resulting from the intermediate treatment is passed to the reaction stage (R2) which has a single reactor.

In addition to the stream or streams (PI1), at least one further feed stream comprising, for example, at least one solvent or organic compound or at least one hydroperoxide or a mixture of two or more thereof can generally be additionally introduced into the reactor or reactors of stage (R2).

For the purposes of the present invention, the term "reactors connected in parallel" includes assemblies in which at least one of the parallel branches of the assembly has at least two reactors connected in series. If a reaction stage has no reactors connected in parallel, it is possible for this reaction stage to be an assembly in which at least two reactors are connected in series.

Depending on the duration of the reaction of organic compound with hydroperoxide in the presence of a catalyst, the catalyst activity or/and the catalyst selectivity will drop to values which are no longer economically justifiable. In such a case, the catalyst having reduced activity or/and selectivity is regenerated.

The present invention therefore also provides a process as described above in which at least one of the catalysts present in the at least two parallel reactors is regenerated during the process.

All possible methods of regeneration are conceivable. In particular, use is made of the regeneration processes described in WO 98/55228, EP-A 0 790 075, EP-A 0 743 094, JP-3-114536, Proc. 7th Intern. Zeolite Conf., Tokyo, 1986, p. 129 ff., in particular pages 134 and 135, and WO 98/18556, which are hereby fully incorporated by reference into the present application.

However, it should be ensured, in particular, that the continuous process for reacting the organic compound with hydroperoxide does not have to be interrupted, since otherwise the process throughput can sometimes be considerably reduced.

The present invention therefore also provides, in a preferred embodiment, a process as described above in which the catalyst regeneration is carried out in such a way that at least one of the parallel reactors is decoupled from the respective reaction stage and the catalyst present in this reactor is regenerated, so that at least one reactor in each reaction stage is always available for the reaction of organic compound with hydroperoxide during the course of the continuous process.

As regards the in-principle procedure for carrying out such a regeneration while continuing the reaction, U.S. Pat. No. 5,849,937 is hereby incorporated by reference.

If, for example, two or more reactors connected in series are used, as described above, in a parallel branch of a reaction stage, it is possible to decouple the entire parallel branch from the reaction stage. It is likewise possible to decouple only one of the reactors connected in series from the process for the regeneration of the catalyst present therein. If, for example, in a specific arrangement, the number of reactors decoupled from a reaction stage for regeneration of the catalysts present therein is such that only one of the parallel branches remains in the continuous process, then, particularly preferably in the case of the remaining branch comprising cascaded reactors, all of the reactors connected in series remain in the process so that the continuous process is not interrupted.

The time for which a catalyst remains in operation for reacting an organic compound with hydroperoxide in the process of the present invention before the reactor has to be decoupled from the reaction stage concerned for regeneration of the catalyst, can be chosen freely for the purposes of the present invention. This operating time is preferably at least 500 hours, more preferably at least 700 hours, in particular at least 900 hours and particularly preferably at least 1100 hours. For the purposes of the present invention, the term "operating time" refers to the period of time in which organic compound is reacted with hydroperoxide in the reactor concerned.

The time for which the reactor is taken out of operation from the reaction stage concerned for regeneration of the catalyst present in this reactor is preferably less than 350 hours, more preferably less than 300 hours and particularly preferably less than 250 hours. This regeneration time covers the entire period of time between the point in time at which the reactor is decoupled from the reaction stage concerned and the point in time at which the reactor containing the regenerated catalyst is coupled back into the reaction stage concerned.

In a further preferred embodiment, the process of the present invention is carried out so that at all times only one of the parallel reactors of a reaction stage is decoupled from the process in order to regenerate the catalyst.

Accordingly, the present invention also provides a process as described above in which x−1 reactors of x reactors connected in parallel in a reaction stage are always available for the reaction of organic compound with hydroperoxide.

Here, x is as defined above and is >1.

For the purposes of the present invention, the term "reactors connected in parallel" also encompasses assemblies in which at least one of the reactors connected in parallel has not only one but two or more reactors connected to one another. In particular, the term "reactors connected in parallel" encompasses assemblies in which at least one of the reactors connected in parallel comprises a series arrangement of two or more reactors.

A preferred process in the context of the present invention is, for example, one in which the reaction stage (R1) has x reactors connected in parallel, each product stream from these reactors is fed separately to an intermediate treatment (I1) and each stream (PI1) from each intermediate treatment is introduced into one of x parallel reactors of stage (R2).

This process is preferably carried out by firstly reacting hydroperoxide with the organic compound in one of the parallel branches, bringing a second of the parallel branches into operation after a particular time interval and bringing the third, if present, of the parallel branches into operation after another interval of time. The time intervals between these start-up operations are very particularly preferably selected so that each of the parallel branches can be taken out of operation in the process when the catalyst present in the respective reactors no longer has the necessary activity or/and selectivity but the other catalysts are still sufficiently active or/and selective. Knowledge of the catalyst properties and thus the ability to determine the appropriate time intervals precisely and, for example, to match the reaction conditions, reactor sizes or/and number of parallel branches employed to the regeneration times for the catalyst makes it possible for a person skilled in the art to use this time-offset start-up procedure to operate a particularly efficient process in which, particularly preferably, x−1 branches of x parallel branches are always effectively and efficiently available. Of course, this time-offset procedure is also possible when only one of the reaction stages (R1) and (R2) has x parallel reactors.

Of course, the apparatus and the process described in the context of the present invention are not restricted to one reaction stage (R1), one intermediate treatment (I1) and one reaction stage (R2). Further reaction stages and further intermediate treatment stages in all combinations are likewise possible. Accordingly, for example, reaction stage (R2) can be followed directly by a reaction stage (R3) and this can in turn be followed by a reaction stage (R4). Likewise, (R2) can be followed by an intermediate treatment (I2) and this can be followed by a further intermediate treatment (I3) with subsequent reaction stage (R3) or (I2) can be followed directly by a reaction stage (R3). The type of intermediate treatment can be the same as that of (I1) or be different from (I1). As far as the reaction stages (R3) and (R4) and so on are concerned, reactions of hydroperoxide with organic compound can likewise take place in these stages, but other reactions are also conceivable. For example, the destruction of excess hydroperoxide can be provided in stage (R3).

Accordingly, the present invention also provides a process as described above which comprises at least one further intermediate treatment and at least one further reaction stage.

As regards the reactor assemblies in the further reaction stages or the arrangement of the apparatuses in the further intermediate treatments, all conceivable embodiments are possible. In particular, reference may be made to the above-described arrangements described in the context of (R1), (R2) and (I1). As regards the combination or division of streams from the reaction stages (R2), (R3) and so forth or from the intermediate treatments (I2) and so forth, it is also possible to use all suitable embodiments. In particular, reference may be made to the abovedescribed embodiments described in the context of (R1), (R2) and (I1).

The reaction of the organic compound with the hydroperoxide in stage (R1) takes place, as described in detail above, in at least one reactor suitable for this purpose. Starting materials for the reaction are the organic compound to be reacted, the hydroperoxide and, if appropriate, one or more solvents which are suitable for and/or necessary in the reaction.

In the process of the present invention, preference is given to introducing a feed stream comprising hydroperoxide, the organic compound to be reacted and at least one suitable solvent into the reactor or reactors of (R1). A stream in which the concentrations of the individual components of the stream are selected so that the stream is liquid and consists of a single phase is preferred.

If desired, at least one basic compound, at least one acidic compound or at least one neutral compound or a mixture of two or more of these compounds may be added to the feed stream prior to introduction into a reactor of (R1). Preference is given to adding, for example, a basic compound. Examples of basic compounds are those mentioned below in the context of the base addition in at least one intermediate treatment.

As solvents, it is in principle possible to use all solvents which are suitable for the respective reaction. Preference is given, for example, to water, alcohols, preferably lower alcohols, more preferably alcohols having less than 6 carbon atoms, for example methanol, ethanol, propanols, butanols, pentanols, diols or polyols, preferably ones having less than 6 carbon atoms, ethers such as diethyl ether, tetrahydrofuran, dioxane, 1,2-diethoxyethane, 2-methoxyethanol, esters such as methyl acetate or butyrolactone, amides such as dimethylformamide, dimethylacetamide, N-methylpyrrolidone, ketones such as acetone, nitriles such as acetonitrile or mixtures of two or more of the abovementioned compounds.

Preference is given to using methanol as solvent in the reaction of hydroperoxide with organic compound.

The hydroperoxide concentrations employed in the feed stream or streams are preferably in the range from 0.01 to 10% by weight, particularly preferably from 0.1 to 9% by weight, more particularly preferably from 1 to 8% by weight and in particular from 5 to 7% by weight.

Depending on the temperature chosen for the reaction of the organic compound with the hydroperoxide in (R1), it may be useful to preheat the feed stream or streams prior to entry into the reactor of (R1) in the process of the present invention.

The mixture resulting from (R1) is conveyed in at least one product stream (P1) to the intermediate treatment (I1).

While, as described above, all suitable intermediate treatments are conceivable, intermediate treatment stages used in the process of the present invention are preferably processes in which unreacted hydroperoxide is separated from a product stream resulting from the reaction of the organic compound with hydroperoxide or in which base is added to a product stream.

Accordingly, the present invention also provides a process as described above in which at least one intermediate treatment is separation of the hydroperoxide from at least one product stream by distillation or addition of a base to a product stream.

As regards the addition of base, it is in principle possible to use all suitable procedures. Thus, for example, the base can be preheated before addition. Likewise, the base can be mixed with the product stream in a suitable manner during the addition.

As bases, it is possible to add all suitable basic compounds. Particular preference is given to using basic compounds which influence the reaction of hydroperoxide with the organic compound in a desirable way in the process of the present invention. If, for example, zeolites are used as heterogeneous catalysts, as described in detail below, then preference is given to using basic compounds which reduce the acidity of these zeolites.

For example, ammonium salts, alkali metal salts, especially lithium, sodium and potassium salts, and also alkaline earth metal salts are conceivable. The anions of these salts include, for example, halides such as chloride and bromide, nitrate, sulfate or hydroxide and also the anions of phosphorus-, arsenic-, antimony- and tin-containing acids, e.g. perchlorate, phosphate, hydrogenphosphate, dihydrogenphosphate, arsenate and stannate. Other anions such as formate, acetate, hydrogencarbonate or carbonate are also conceivable.

Particular mention may here be made of strong and weak bases. As strong bases, sodium hydroxide or potassium hydroxide, for example, are possible. Weak bases which may be mentioned are, for example, ammonium hydroxide, carbonates, hydrogencarbonates and hydrogenphosphates of lithium, sodium and potassium, e.g. ammonium hydroxide, sodium carbonate, sodium hydrogencarbonate, potassium carbonate, lithium carbonate, potassium hydrogencarbonate, lithium hydrogencarbonate, potassium hydrogenphosphate, salts of carboxylic acids having from 1 to 10 carbon atoms, e.g. alkali metal salts or alkaline earth metal salts or alkoxides of alcohols having from 1 to 10 carbon atoms, e.g. alkaline earth metal alkoxides.

The amount of base added can essentially be chosen freely for the purposes of the process of the present invention and can be matched to the respective requirements. Preference is given to adding such an amount of base that not more than 10 mmol of base, more preferably not more than 5 mmol of base, particularly preferably not more than 2 mmol of base and very particularly preferably less than 1 mmol of base, are/is present per mole of hydroperoxide.

In the context of an intermediate treatment, preference is likewise given to removing hydroperoxide from a product stream, where this hydroperoxide is unreacted hydroperoxide from the preceding reaction stage. It is also possible, in the context of an intermediate treatment, to provide two or more separation stages which may be arranged in parallel or/and in series. In a series arrangement, it is conceivable, for example, to separate unreacted hydroperoxide from the preceding reaction stage substantially from the product stream resulting from this reaction stage in a first separation stage and, in at least one further separation stage, to separate hydroperoxide once more from the reaction mixture which results after the substantial removal of hydroperoxide and still contains residual hydroperoxide.

In the process of the present invention, the separation of the hydroperoxide can be carried out in one or more intermediate treatments and can be carried out by all customary methods of the prior art. Here, it is also possible to use different separation methods in different separation stages. In the context of an intermediate treatment, it is also possible, as mentioned above, for a plurality of separation stages to be provided.

The hydroperoxide is preferably separated off by distillation. Depending on the requirements of the process, separation in one or more distillation columns is possible. Preference is given to using one distillation column for separating off the hydroperoxide in a separation stage.

In the process of the present invention, it is conceivable for a dedicated separation apparatus to be provided for each stage in which the hydroperoxide is separated off. It is likewise possible, in the case of an appropriate reaction procedure and a plurality of separation stages, to carry out the separations in a single separation apparatus.

If a plurality of separation stages are provided, it is also possible, by means of an appropriate reaction procedure, to carry out two or more separation stages in a single separation apparatus. Accordingly, it is quite generally possible for a total of m separation apparatuses to be provided for n separation stages, where $1 \leq m \leq n$.

Should a further separation of hydroperoxide be desired subsequent to the last stage in which a reaction of the organic compound with the hydroperoxide takes place, for example in order to recycle any residual hydroperoxide, this is of course likewise possible in the context of the process of the present invention.

In the process of the present invention, it is possible, in one or more separation apparatuses, not only to separate the hydroperoxide from the mixture resulting from a reaction stage in which the organic compound is reacted with the hydroperoxide but also to separate the reacted organic compound or/and the unreacted organic compound from this mixture. It is naturally also possible, after the hydroperoxide has been separated off, to transfer the remaining reaction product into a further separation apparatus specifically provided for this purpose and there to separate the reacted organic compound or/and the unreacted organic compound from the reaction product.

In both cases, it is possible, for example, to collect the reacted organic compound or/and the unreacted organic compound in the n separation apparatuses and to separate it/them off after the reaction of the organic compound with the hydroperoxide is complete.

Preference is given to separating off the reacted organic compound and further preference is given to separating it off in addition to the hydroperoxide in the respective separation apparatus. In a separation by distillation, it is possible, for example, to take off the reacted organic compound at the top and to separate the hydroperoxide from the mixture via a side offtake.

In the process of the present invention, it is naturally likewise possible, when using a distillation unit as separation apparatus, to separate the hydroperoxide from the mixture not via a side offtake but at the bottom.

If the hydroperoxide and/or the reacted organic compound is separated off in a distillation unit, it is possible, in the process of the present invention, for any high-boiling components of the mixture formed as by-products in the reaction of the organic compound with the hydroperoxide to be separated off at the bottom. It is also possible to lower the bottom temperature, for example by addition of preferably gaseous, low-boiling components such as the organic compound itself, for example preferably propene.

Examples of such low-boiling components are hydrocarbons having from 1 to 4 carbon atoms, for example methane, ethane, propane, butane, ethene or butenes. It is likewise possible to use, for example, nitrogen or argon.

It is of course also possible in the process of the present invention, for example in (R1) or/and (R2) or in one or more further reaction stages, to react a plurality of organic compounds with the hydroperoxide. It is likewise conceivable for a plurality of hydroperoxides to be used for the reaction.

If a plurality of organic compounds and/or a plurality of hydroperoxides are reacted with one another in the respective stages, various products resulting from the reactions may be present in the mixtures or product streams resulting from the respective reaction stages. If these are in turn separated off by distillation in the respective separation stages, it may be necessary to provide a plurality of distillation columns for the separation. Likewise, the separation of a plurality of hydroperoxides from the mixture by distillation can make it necessary to employ a plurality of distillation columns.

If reacted organic compound is also separated off in such a distillation stage, the distillation is generally carried out in such a way that at least 50%, preferably at least 60%, more preferably at least 70%, particularly preferably at least 80% and very particularly preferably at least 90%, of the reacted organic compound is separated off from a product stream (P1).

The separation is preferably carried out so that a liquid mixture comprising the hydroperoxide is separated off. It is possible for the hydroperoxide-containing mixture which is separated off to further comprise, for example, small amounts of unreacted organic compound and/or reacted organic compound in addition to the hydroperoxide. Likewise, the mixture in which the hydroperoxide which has been separated off is present may further comprise any solvent which may be required.

If the reacted organic compound is also separated off in (I1), this separation, from which a liquid mixture or a liquid/gas mixture is preferably obtained, results in a stream comprising not only the reacted organic compound but possibly also the unreacted organic compound and/or small amounts of solvent.

If, as described above, the separation is carried out in a distillation unit and high-boiling components are separated from (P1) at the bottom, this separation results in a stream comprising the high-boiling components, which may, for example, be by-products of the reaction in (R1).

If a fractional distillation as described above is carried out in the intermediate treatment (I1), various product streams (PI1) can be fed to the stage (R2) in which organic compound is likewise reacted with hydroperoxide.

For example, a product stream (PI1) comprising hydroperoxide which has been separated off can be passed to the stage (R2) in which this hydroperoxide is reacted with organic compound. The organic compound or compounds used here can be identical to or different from the organic compound which was reacted in (R1). Preferably, the organic compound used in (R1) is also used in (R2). It is also conceivable for, in (R2), the product stream (PI1) comprising hydroperoxide which has been separated off to be brought into contact with a further product stream (PI1) comprising unreacted organic compound which has been separated off. In addition to these streams, further hydroperoxide or further organic compound or both further hydroperoxide and further organic compound can be added in (R2). The terms "further hydroperoxide" and "further organic compound" refer, for the purposes of the present invention, to hydroperoxide and organic compound, respectively, which have not been used in stage (R1). Likewise, a product stream (PI1) comprising hydroperoxide which has been separated off can, in (R2), be brought into contact exclusively with further organic compound so that the organic compound is reacted with hydroperoxide. Furthermore, it is also possible for a product stream (PI1) comprising unreacted organic compound which has been separated off to be brought into contact with further hydroperoxide and reacted with the hydroperoxide.

If hydroperoxide is separated from (P1) in the intermediate treatment (I1), a particularly preferred embodiment of the process of the present invention comprises feeding at least one stream (PI1) comprising hydroperoxide which has not been reacted in (R1) and has been separated off to the stage (R2) and bringing it into contact, in (R2), with organic compound which does not result from (R1) and is particularly preferably freshly introduced into the process.

As described above, it is conceivable for various processes to be employed in the intermediate treatment (I1). Accordingly, for example, it is possible to provide at least one separation apparatus and, in addition, at least one addition of base in (I1). In such an intermediate treatment, it is possible, for example, for unreacted hydroperoxide in the product stream (P1) to be separated from (P1), resulting in a product stream (PI1) comprising hydroperoxide, for base to be added to this product stream (PI1) and for the resulting new product stream (PI1) comprising hydroperoxide and base to be passed to the reaction stage (R2).

If organic compound is reacted with hydroperoxide in (R1), hydroperoxide which has not been reacted in (R1) is separated from (P1) in (I1) to give (PI1), (PI1) is introduced into (R2) and organic compound is again reacted with hydroperoxide there, the reaction conditions in (R1) in the process of the present invention are preferably chosen so that the hydroperoxide conversion is generally in the range from 70 to 95%, preferably in the range from 80 to 94.5% and particularly preferably in the range from 85 to 94%.

Furthermore, pressure, temperature and residence time of the reaction mixture in (R1) are preferably chosen so that the mixture resulting from the reaction is liquid and consists of a single phase.

The pressures chosen are generally in the range from autogenous pressure to 100 bar, preferably in the range from autogenous pressure to 40 bar and particularly preferably in the range from autogenous pressure to 30 bar.

The temperatures in (R1) are generally in the range from 0 to 120° C., preferably in the range from 10 to 100° C., more preferably in the range from 20 to 90° C. and particularly preferably in the range from 25 to 80° C.

The concentration of the organic compound to be reacted is, for example, chosen so that the molar ratio of organic compound to be reacted: hydroperoxide is in the range from 0.7 to 20, preferably in the range from 0.8 to 5.0, more particularly preferably in the range from 0.9 to 2.0 and in particular in the range from 1.0 to 1.6.

In (R2), the concentration of the organic compound to be reacted is then chosen so that the molar ratio of organic compound to be reacted: hydroperoxide is preferably in the range from 0.7 to 20, more preferably in the range from 0.8 to 5.0, particularly preferably in the range from 0.9 to 2.0 and in particular in the range from 1.0 to 1.6.

In this case, the reaction in (R2) is carried out at a pressure, temperature and residence time of the reaction mixture which are such that hydroperoxide conversions which are generally in the range of $\geq 90\%$, preferably in the range of $\geq 92\%$, more preferably in the range of $\geq 95\%$ and particularly preferably in the range from 95 to 99.5%, are achieved.

Here, the pressures chosen are generally in the range from autogenous pressure to 100 bar, preferably in the range from autogenous pressure to 40 bar and particularly preferably in the range from autogenous pressure to 30 bar.

The temperatures are generally in the range from 0 to 120° C., preferably in the range from 10 to 100° C., more preferably in the range from 20 to 90° C. and particularly preferably in the range from 25 to 80° C.

The residence times of the reaction mixture in (R1) or/and (R2) can essentially be determined without restriction and can, for example, be matched to the desired conversions, as described above. In general, they are less than 5 hours, preferably less than 3 hours, more preferably less than 1 hour and particularly preferably about half an hour.

As described above, the process of the present invention can comprise at least one further intermediate treatment in addition to (I1) and at least one further reaction stage in addition to (R1) and (R2). In a particularly preferred embodiment, the process of the present invention comprises reaction stages (R1) and (R2) each having at least two reactors connected in parallel, an intermediate treatment (I1) in which base is added, an intermediate treatment (I2) in which hydroperoxide is separated from the product stream (P2) and a reaction stage (R3).

The present invention accordingly provides a process as described above in which in the reaction stage (R1), hydroperoxide is reacted with organic compound in at least two reactors connected in parallel in the presence of a catalyst to give at least one product stream (P1) comprising unreacted hydroperoxide, unreacted organic compound and reacted organic compound, in the intermediate treatment (I1), base is added to the product stream or streams (P1) to give at least one product stream (PI1), in the reaction stage (R2), unreacted hydroperoxide and unreacted organic compound present in the product stream or streams (PI1) are reacted in at least two reactors connected in parallel to give at least one product stream (P2) comprising unreacted hydroperoxide, in an intermediate treatment (I2), unreacted hydroperoxide is separated by distillation from the product stream or streams (P2) to give at least one product stream (PI2) comprising hydroperoxide, and the hydroperoxide present in the product stream or streams (PI2) is reacted with organic compound in a reaction stage (R3) to give at least one product stream (P3).

If, in this process, base is added in the intermediate treatment (I1), then all procedures are possible in principle. One preferred method of carrying out the intermediate treatment (I1) is to add base separately to each product stream (P1) so that each product stream (P1) results in a product stream (PI1) and to introduce each of these product streams (PI1) into a different reactor of the reaction stage (R2). Another preferred method is one in which the product streams (P1) are combined to form a single stream, base is added to this single stream and the resulting stream (PI1) is divided into a plurality of streams which are, again preferably, each introduced into a different reactor of the reaction stage (R2). Here, in a further preferred embodiment, the number of parallel reactors in (R1) corresponds to the number of parallel reactors in (R2) and therefore the number of streams into which the product stream (PI1) is divided corresponds to the number of product streams (P1) resulting from (R1).

In a preferred embodiment, the distillation step in which, in accordance with the above-described preferred process, unreacted hydroperoxide is separated from the product stream or streams (P2) is carried out in such a way that, should two or more product streams (P2) result from (R2), these are combined to form a single stream and this single stream is fed to a suitable distillation apparatus, as described above, preferably resulting in a product stream (PI2) comprising hydroperoxide.

In this preferred embodiment of the process of the present invention, the pressures chosen in (R1), (R2) and (R3) are generally in the range from autogenous pressure to 100 bar, preferably in the range from autogenous pressure to 40 bar and particularly preferably in the range from autogenous pressure to 30 bar. The pressures can here be the same in all 3 reaction stages or the pressures in the reaction stages can be different.

In this preferred embodiment, the temperatures in (R1), (R2) and (R3) are generally in the range from 0 to 120° C., preferably in the range from 10 to 100° C., more preferably in the range from 20 to 90° C. and particularly preferably in the range from 25 to 80° C. The temperatures can here be the same in all 3 reaction stages or the temperatures in the reaction stages can be different.

In this preferred embodiment, the concentration of the organic compound to be reacted in (R1), (R2) and (R3) is selected so that the molar ratio of organic compound to be reacted: hydroperoxide is preferably in the range from 0.7 to 20, more preferably in the range from 0.8 to 5.0, particularly preferably in the range from 0.9 to 2.0 and in particular in the range from 1.0 to 1.6. The respective molar ratios in (R1), (R2) and (R3) can be identical or different.

In this preferred embodiment, the reaction in (R1) is carried out at a pressure, temperature and residence time of the reaction mixture which are such that hydroperoxide conversions which are generally in the range of $\geq 50\%$, preferably in the range of $\geq 60\%$, more preferably in the range of $\geq 70\%$ and particularly preferably in the range from 70 to 80%, are achieved.

In this preferred embodiment, the reaction in (R2) is carried out at a pressure, temperature and residence time of the reaction mixture which are such that hydroperoxide conversions which are generally in the range of $\geq 80\%$, preferably in the range of $\geq 85\%$ and particularly preferably in the range from 87 to 93%, are achieved.

In this preferred embodiment, the reaction in (R3) is carried out at a pressure, temperature and residence time of the reaction mixture which are such that hydroperoxide conversions which are generally in the range of $\geq 98\%$ and particularly preferably in the range from 99 to 99.99% are achieved.

In this preferred embodiment in which base is added in the intermediate treatment (I1) and hydroperoxide is separated off in the intermediate treatment (I2), the reaction conditions chosen in reaction stage (R2) are essentially the same as those in reaction stage (R1). As reaction conditions in stage (R3), preference is given to those described in detail above for the preferred embodiment in which organic compound is reacted with hydroperoxide in (R1), hydroperoxide is separated off in (I1) and organic compound is reacted with hydroperoxide in (R2).

Possible reactors are all conceivable reactors which are best suited to the respective reactions in the respective reaction stages. In the process of the present invention, a reactor does not have to be a single vessel. Rather, it is also possible, for example, for a cascade of stirred reactors to be used as reactor in (R1) or (R2) or a further reaction stage. Preference is given to using fixed-bed reactors as reactors in the process of the present invention.

Accordingly, the present invention also provides a process as described above in which fixed-bed reactors, preferably isothermal fixed-bed reactors, are used as reactors.

In the process of the present invention, particular preference is given to isothermal fixed-bed reactors which are preferably used when an organic compound is reacted with hydroperoxide in (R1) or/and (R2) without hydroperoxide being separated off in an intermediate treatment. Adiabatic fixed-bed reactors are preferably used when hydroperoxide which has not been reacted in (R1) and has been separated off is reacted with organic compound, for example in (R2) or in (R3).

The present invention therefore also provides an apparatus comprising at least two isothermal fixed-bed reactors connected in parallel, a separation apparatus and at least one adiabatic fixed-bed reactor.

In particular, the present invention provides an apparatus comprising at least two isothermal fixed-bed reactors connected in parallel, at least two apparatuses for the addition of basic compound, at least two further isothermal fixed-bed reactors connected in parallel, at least one separation apparatus and at least one adiabatic fixed-bed reactor.

The fixed-bed reactors used are more preferably fixed-bed tube reactors or fixed-bed shell-and-tube reactors, with, if hydroperoxide which has not been reacted in (R1) is reacted with organic compound in, for example, (R2) or (R3), tube reactors preferably being used in (R2) or (R3) and shell-and-tube reactors preferably being used in (R1). In the above-described preferred embodiment in which base is added in (I1) and the product stream is worked up by distillation in (I2), preference is given to using shell-and-tube reactors in (R1) and (R2) and tube reactors in (R3).

The present invention likewise provides for the use of this apparatus for reacting an organic compound with a hydroperoxide.

Hydroperoxides which can be used in the process of the present invention are all hydroperoxides which are known from the prior art and are suitable for the reaction with the organic compound.

Examples of such hydroperoxides are tert-butyl hydroperoxide and ethylbenzene hydroperoxide, which are mentioned in the above-cited SRI Report 2E "Propylene Oxide". Here, tert-butyl hydroperoxide is prepared from isobutane and oxygen, and ethylbenzene hydroperoxide is prepared from ethylbenzene and oxygen.

Preference is given to using hydrogen peroxide as hydroperoxide in the present process. Accordingly, the present invention also provides a process as described above in which hydrogen peroxide is used as hydroperoxide. Preference is given to using an aqueous hydrogen peroxide solution.

Hydrogen peroxide can be prepared, for example, by the anthraquinone process by means of which virtually the entire world production of hydrogen peroxide is prepared. This process is based on the catalytic hydrogenation of an anthraquinone compound to form the corresponding anthrahydroquinone compound, followed by reaction of this with oxygen to form hydrogen peroxide and subsequent extraction to separate off the hydrogen peroxide formed. The anthraquinone compound obtained back is hydrogenated again to close the catalysis cycle.

An overview of the anthraquinone process is given in "Ullmanns Encyclopedia of Industrial Chemistry", 5th edition, Volume 13, pages 447 to 456.

Another possible method of obtaining hydrogen peroxide involves conversion of sulfuric acid into peroxodisulfuric acid by anodic oxidation with simultaneous evolution of hydrogen at the cathode. Hydrolysis of the peroxodisulfuric acid then leads via peroxosulfuric acid to hydrogen peroxide and sulfuric acid, which can thus be recovered.

It is of course also possible to prepare hydrogen peroxide from hydrogen and oxygen.

Before the use of hydrogen peroxide in the process of the present invention, it is possible to free, for example, a commercially available hydrogen peroxide solution of undesirable ions. This can be achieved using, inter alia, methods as are described, for example, in WO 98/54086, DE-A 42 22 109 or WO 92/06918. It is likewise possible for at least one salt present in the hydrogen peroxide solution to be removed from the hydrogen peroxide solution by means of ion exchange in an apparatus containing at least one nonacidic ion exchange bed having a cross-sectional area of flow A and a height H, where the height H of the ion-exchange bed is less than or equal to $2.5 \times A^{1/2}$, in particular less than or equal to $1.5 \times A^{1/2}$. For the purposes of the present invention, it is in principle possible to use all nonacidic ion exchange beds containing cation exchangers and/or anion exchangers. Within an ion exchange bed, cation and anion exchangers can also be used as so-called mixed beds. In a preferred embodiment of the present invention, only one type of nonacidic ion exchangers is used. Further preference is given to the use of a basic ion exchanger, particularly preferably a basic anion exchanger and more particularly preferably a weakly basic anion exchanger.

As catalysts for the reaction of the organic compound with hydroperoxide, it is in principle possible to use all catalysts, preferably heterogeneous catalysts, which are suitable for the respective reaction. Preference is here given to using catalysts which comprise a porous oxidic material such as a zeolite. Catalysts comprising a titanium-, vanadium-, chromium-, niobium- or zirconium-containing zeolite as porous oxidic material are preferably used.

In particular, there are zeolites which contain no aluminum and in which the Si(IV) in the silicate lattice is partly replaced by titanium as Ti(IV). The titanium zeolites, in particular those having a crystal structure of the MFI type, and possible methods of preparing them are described, for example, in EP-A 0 311 983 or in EP-A 0 405 978.

Titanium zeolites having an MFI structure can, as is known, be identified by means of a particular X-ray diffraction pattern and also by means of a lattice vibration band in the infrared (IR) region at about 960 cm$^{-1}$ and in these ways differ from alkali metal titanates or crystalline and amorphous TiO$_2$ phases.

Specific mention may be made of titanium-, vanadium-, chromium-, niobium- and zirconium-containing zeolites having a pentasil zeolite structure, in particular the types which can be assigned X-ray-crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG, ZON structures and to mixed structures comprising two or more of the abovementioned structures. In the process of the present invention, it is also possible to use titanium-containing zeolites having the UTD-1, CIT-1 or CIT-5 structure. Further titanium-containing zeolites which may be mentioned are those having the ZSM-48 or ZSM-12 structure. The titanium-containing structures RUB-29, RUB-30, RUB-31 and RUB-23 may likewise be mentioned.

In the process of the present invention, particular preference is given to Ti zeolites having an MFI or MEL structure or a mixed MFI/MEL structure. Further preference is given specifically to the Ti-containing zeolite catalysts which are generally referred to as "TS-1", "TS-2", "TS-3" and also Ti zeolites having a framework structure isomorphous to β-zeolite.

Very particular preference is given to using a heterogeneous catalyst comprising titanium-containing silicalite TS-1 in the process of the present invention.

It is possible, in the process of the present invention, to use the porous oxidic material itself as catalyst. However, it is of course also possible for the catalyst used to be a shaped body comprising the porous oxidic material. Here, it is possible to use, starting from the porous oxidic material, all processes of the prior art for producing the shaped body.

Among the reactions which are possible in the process of the present invention, mention may be made by way of example of the following:

the epoxidation of olefins, e.g. the preparation of propene oxide from propene and H$_2$O$_2$ or from propene and mixtures which supply H$_2$O$_2$ in situ;

hydroxylations such as the hydroxylation of monocyclic, bicyclic or polycyclic aromatics to form monosubstituted, disubstituted or higher-substituted hydroxy aromatics, for example the reaction of phenol and H$_2$O$_2$ or of phenol and mixtures which supply H$_2$O$_2$ in situ to give hydroquinone;

oxime formation from ketones in the presence of H$_2$O$_2$ or mixtures which supply H$_2$O$_2$ in situ and ammonia (ammonoximation), for example the preparation of cyclohexanone oxime from cyclohexanone;

the Baeyer-Villiger oxidation.

In the process of the present invention, preference is given to reacting organic compounds which have at least one C—C double bond. Accordingly, the present invention provides a process as described above in which the organic compound has at least one C—C double bond.

As examples of such organic compounds having at least one C—C double bond, mention may be made of the following alkenes.

Ethene, propene, 1-butene, 2-butene, isobutene, butadienes, pentenes, piperylene, hexenes, hexadienes, heptenes, octenes, diisobutene, trimethylpentene, nonenes, dodecene, tridecene, tetradecene to eicosenes, tripropene and tetrapropene, polybutadienes, polyisobutenes, isoprene, terpenes, geraniole, linaloole, linalyl acetate, methylenecyclopropane, cyclopentene, cyclohexene, norbornene, cycloheptene, vinylcyclohexene, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenoles, butenediols, cyclopentenediols, penteneols, octadieneols, trideceneols, unsaturated steroids, ethoxyethene, isoeugenole, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils.

In the process of the present invention, preference is given to using alkenes containing from 2 to 8 carbon atoms. Ethene, propene and butene are particularly preferably reacted. Very particular preference is given to reacting propene.

The present invention therefore also provides a process as described above in which hydrogen peroxide is reacted with alkene, preferably propene, to give alkene oxide, preferably propylene oxide, using as catalyst a zeolite catalyst, preferably a titanium silicalite catalyst, in particular a titanium silicalite catalyst having the TS-1 structure.

In the reaction of hydrogen peroxide with alkylene, preferably propene, to give alkylene oxide, preferably propylene oxide, the solvent used can be any suitable solvents. Preference is given to using organic solvents, such as alcohol, single or as a mixture of thwo or more thereof. Also it is possible to use an alcohol/water-mixture. Particularly preference is given to using methanol as a solvent in this reaction.

The amount of the used solvent is variable in wide ranges. Possible amounts lie between 5 and 25 g methanol per gram hydrogen peroxide used. Preferably is given to using solvent in an amount of 8 to 16 g methanol per gram hydrogen peroxide used, particularly preferred an amount of 10 to 14 g methanol is used per gram hydrogen peroxide used.

As described above, at least one catalyst present in at least one of the reactors connected in parallel is regenerated, preferably in such a way that the continuous process is not interrupted. The decoupling of the reactor or reactors in which the catalyst to be regenerated is present from the process train can here be carried out using any suitable methods.

Particular preference is given to a method of decoupling the reactor or reactors in which the decoupled reactor is not removed from the assembly but remains in place and the catalyst is regenerated in the isolated state. Here, the inflow and outflow lines present are closed off by appropriate measures, for example by means of valves or by physical disconnection and blanking-off of these lines by means of, for example, isolation plates.

Should one or more regeneration gases as described, for example, in one of the processes listed below be required for regenerating the catalyst, the lines required for introduction of these gases are preferably connected after disconnection of the above-described inflow and outflow lines.

Should heating of the reactor and its contents be necessary for the purposes of regeneration, this heating is preferably carried out after the feed lines for the regeneration gases have been connected. The removal of these feed lines is preferably carried out when, should this be necessary, the reactor has cooled down again.

After the reactor has been decoupled from the process train, the catalyst present in the reactor can be regenerated by any suitable methods of the prior art. In particular, it is possible to remove the catalyst from the reactor, to regenerate it and to reinstall it. The catalyst is preferably regenerated in the reactor. The regeneration method can be chosen according to the type of catalyst. In the case of the zeolite catalysts which are used in the particularly preferred process, the following possible methods of regeneration may be mentioned by way of example:

1. A process which involves heating an exhausted catalyst at a temperature of less than 400° C. but higher than 150° C. in the presence of molecular oxygen for a period which is sufficient to increase the activity of the exhausted catalyst, as described in EP-A 0 743 094;
2. A process which involves heating an exhausted catalyst at from 150° C. to 700° C. in the presence of a gas stream containing not more than 5% by volume of molecular oxygen for a period of time which is sufficient to improve the activity of the exhausted catalyst, as described in EP-A 0 790 075;
3. A process in which an exhausted catalyst is treated by heating at from 400 to 500° C. in the presence of an oxygen-containing gas or by washing with a solvent, preferably at a temperature which is from 5° C. to 150° C. higher than the temperature employed during the reaction, as described in JP-A 3 11 45 36;
4. A process in which an exhausted catalyst is treated by calcination at 550° C. in air or by washing with solvents, so that the activity of the catalyst is restored, as described in "Proc. 7th Intern. Zeolite Conf. 1986 (Tokyo)";
5. A process for regenerating a catalyst which comprises the following steps (A) and (B):
   (A) Heating an at least partially deactivated catalyst to a temperature in the range from 250° C. to 600° C. in an atmosphere containing less than 2% by volume of oxygen, and
   (B) Treating the catalyst at a temperature in the range from 250 to 800° C., preferably from 350 to 600° C., with a gas stream containing from 0.1 to 4% by volume of an oxygen-supplying substance or of oxygen or of a mixture of two or more thereof,
   where the process may further comprise the additional steps (C) and (D)
   (C) Treating the catalyst at a temperature in the range from 250 to 800° C., preferably from 350 to 600° C., with a gas stream comprising from >4 to 100% by volume of an oxygen-supplying substance or of oxygen or of a mixture of two or more thereof,
   (D) Cooling the regenerated catalyst obtained in step (C) in an inert gas stream containing up to 20% by volume of a vapor of a liquid selected from the group consisting of water, alcohols, aldehydes, ketones, ethers, acids, esters, nitrites, hydrocarbons and mixtures of two or more thereof.

Details of this process may be found in DE-A 197 23 949.8;

6. A process in which an exhausted catalyst is regenerated by thermal treatment under a gas stream at at least 130° C. in such a way that the time for which the gas stream is present over the catalyst does not exceed 2 hours. Details of this process may be found in WO 98/18556.

It is likewise conceivable for the catalyst to be regenerated by washing with at least one hydrogen peroxide solution or with one or more oxidizing compounds. Of course, the above-described methods can also be combined with one another in an appropriate way.

Furthermore, during the reaction of the organic compound with hydroperoxide, the pH or/and the temperature of the reaction medium or/and the pressure under which the reaction takes place can be changed.

Here, the pH of the reaction medium is preferably achieved by changing the pH of the hydroperoxide solution which is added to the reaction medium. In (R1), this can be done, for example, by appropriate treatment of a feed stream containing hydroperoxide solution. If, for example, hydroperoxide solution is separated off in (I1) or/and (I2), the stream comprising the hydroperoxide which has been separated off can be treated in an appropriate manner so as to change the pH.

The pH of the hydroperoxide stream, in particular the hydrogen peroxide solution, can in principle be adjusted by all customary methods. It is only necessary to take care that the addition of acidic or basic compounds or addition of a solution comprising acidic or basic compounds to the hydroperoxide solution does not adversely affect the subsequent reaction of the organic compound with hydroperoxide. In particular, the pH of the hydroperoxide solution is altered by (a) treatment of the hydroperoxide solution with at least one ion exchanger or (b) addition of
   (aa) an acidic compound or
   (bb) a basic compound or
   (cc) a neutral compound or
   (dd) a mixture of two or more thereof to the hydroperoxide solution or (c) a combination of the methods (a) and (b).

Both strongly basic and weakly basic compounds or both strongly acidic and weakly acidic compounds are in principle suitable for this purpose. In particular, the following salts, inter alia, are conceivable:

Ammonium salts, alkali metal salts, especially lithium, sodium and potassium salts, and alkaline earth metal salts. The anions of these salts comprise, for example, halides such as chloride and bromide, nitrate, sulfate or hydroxide or the anions of phosphorus-, arsenic-, antimony- and tin-containing acids such as perchlorate, phosphate, hydrogenphosphate, dihydrogenphosphate, arsenate and stannate. Other anions such as formate, acetate, hydrogencarbonate or carbonate are also conceivable.

Examples which may be mentioned are, inter alia, lithium chloride, lithium bromide, sodium bromide, lithium nitrate, sodium nitrate, potassium nitrate, lithium sulfate, sodium sulfate, potassium sulfate, sodium hydroxide, potassium hydroxide, ammonium hydroxide, sodium carbonate, sodium hydrogencarbonate, potassium carbonate, lithium carbonate, potassium hydrogencarbonate, lithium hydrogencarbonate and potassium hydrogenphosphate and also lithium acetate, magnesium acetate, calcium acetate, barium acetate or ammonium acetate. Mention may likewise be made of carboxylates of carboxylic acids, in particular carboxylic acids having from 1 to 10 carbon atoms, and alkoxides of alcohols having from 1 to 10 carbon atoms. Further examples include ammonium dihydrogenphosphate, sodium dihydrogenphosphate, potassium dihydrogenphosphate and disodium dihydrogenpyrophosphate.

Ion exchangers which can be used here are essentially all ion exchangers known to those skilled in the art, for example organic ion exchangers, for instance those based on polystyrene, or inorganic ion exchangers, for instance hydrotalcites and other sheet silicates which may contain exchangeable carbonate, hydrogencarbonate or hydroxide groups.

Examples of basic ion exchangers which are particularly preferred for the purposes of the present invention are polystyrene resins having tertiary amine groups, for instance the commercially available anion exchangers Lewatit® MP62 and Lewatit® MP63 and also Dowex® MWA/1 and Dowex® AMW-500. The use of, for example, polystyrene resins containing quaternary ammonium groups and having hydroxide counterions is also conceivable. Examples which may be mentioned here are the commercially available ion exchange resins Lewatit® OC-1950 and also Dowex® 1, Dowex® 2, Dowex® 11, Dowex® 21K and Dowex® 550A.

As regards the alteration of the temperature of the reaction medium in which the reaction of the hydroperoxide with the organic compound takes place, essentially all conceivable methods are possible. For example, the temperature of the reaction medium can be controlled via the temperature of at least one feed stream which is introduced into the reaction medium.

The temperature is preferably varied by means of appropriate thermostatting of the reactor or reactors. Here too, all suitable methods can be employed. For example, the reactor or reactors can be provided with a double wall through which there is passed, for example, a liquid via whose temperature the temperature of the reaction medium in the reactor is adjusted. It is of course also possible to provide various zones of the reactor or reactors with separate double walls and thus to pass, for example, liquids having different temperatures around the various zones. The zone temperature control is of course not restricted to embodiments in which the reactor is provided with one or more double walls, but can also be achieved by all other suitable methods.

In a preferred embodiment of the process of the present invention, the hydroperoxide is separated off and is again reacted with alkene to give a crude product mixture from which unreacted alkene is preferably separated off and recirculated to the process as starting material. In a possible embodiment, this crude product is subjected to a distillation in which it is fractionated into a low-boiling fraction comprising alkene and compounds having a boiling point lower than that of the alkene and a high-boiling fraction comprising the alkene oxide and compounds having a boiling point higher than the alkene. In this low-boiling fraction, oxygen accumulates in a concentration which makes the low-boiling fraction an ignitable mixture.

In order to be able to distill the alkene off without danger, it is possible to add an inert substance, preferably methane, having a boiling point lower than that of the alkene, preferably propene, in the upper part of the separation apparatus for separating alkene from the low-boiling mixture by distillation in such an amount that the oxygen is diluted to a concentration at which the mixture is no longer ignitable. It is likewise possible to employ a process for the work-up of a mixture (M1) comprising an alkene and oxygen, in which (i) oxygen is removed from the mixture (M1) by means other than distillation to give a mixture (M2) and (ii) the alkene is separated from the mixture (M2) by distillation.

In the process of the present invention, oxygen is preferably removed by combustion. Preference is likewise given to an embodiment in which the mixture (M1) is subjected to reaction conditions under which the oxygen present in the mixture reacts with a suitable chemical compound. In a preferred embodiment of the process of the present invention, combustion of the oxygen present in the mixture (M1) is carried out using at least one suitable catalyst. All suitable catalysts or catalyst mixtures can be used for this purpose. Preference is given, inter alia, to noble metals such as Pt, Rh or Pd, which can be applied to suitable supports, for example metal oxides. For example, use is made of Pd catalysts supported on $Al_2O_3$. Mention may likewise be made of copper chromite catalysts. Mention may here be made, for example, of the commercially available catalysts R0-25/50 S6, R0-20/47 K2-4 or R3-20 S6 from BASF AG.

In many cases, the crude product from the epoxidation further comprises the alkane corresponding to the alkene. In this case, the oxygen can be removed from a mixture (M1) comprising unreacted oxygen, alkene and alkane obtained as crude product from the epoxidation by oxydehydrogenation of the alkane to give the alkene. The oxydehydrogenation of the alkane or alkanes can be carried out either catalytically or in the absence of catalysts. The oxydehydrogenation is preferably carried out using a suitable catalyst. As regards these catalysts, reference may be made, for example, to M. Xu, J. H. Lunsford, React. Kinet. Catal. Lett. 57 (1996) pp. 3–11 and to B. Delmon, Stud. Surf. Sci. Catal. 110 (1997) pp. 43–59 and the literature references cited therein, which are hereby fully incorporated by reference into the present application.

We claim:

1. A continuous process for reacting an organic compound with hydroperoxide in the presence of a catalyst, wherein the reaction is carried out in a reactor assembly comprising at least two reactors connected in parallel.

2. A continuous process as claimed in claim 1, in which
    the organic compound is reacted with hydroperoxide in the presence of a catalyst in a reaction stage (R1) to give at least one product stream (P1),
    the product stream or streams (P1) is passed to an intermediate treatment (I1) to give, as output from (I1), at least one product stream (PI1) comprising hydroperoxide, and
    the product stream or streams (PI1) is passed to a reaction stage (R2) in which hydroperoxide is reacted with the organic compound in the presence of a catalyst to give at least one product stream (P2),
    wherein at least two reactors connected in parallel are used in at least one of the reaction stages (R1) and (R2).

3. A process as claimed in claim 2, wherein at least one of the catalysts present in the two or more reactors connected in parallel is regenerated during the process.

4. A process as claimed in claim 3, wherein the catalyst regeneration is carried out in such a way that at least one of the parallel reactors is decoupled from the respective reaction stage and the catalyst present in this reactor is regenerated, so that at least one reactor in each reaction stage is always available for the reaction of organic compound with hydroperoxide during the course of the continuous process.

5. A process as claimed in claim 4, wherein x−1 reactors of x reactors connected in parallel in a reaction stage are always available for the reaction of organic compound with hydroperoxide.

6. A process as claimed in claim 4, comprising at least one further intermediate treatment and at least one further reaction stage.

7. A process as claimed in claim 4, wherein at least one intermediate treatment is
    separation of the hydroperoxide from at least one product stream by distillation or
    addition of a base to at least one product stream.

8. A process as claimed in claim 2, wherein
    in the reaction stage (R1), hydroperoxide is reacted with organic compound in at least two reactors connected in parallel in the presence of a catalyst to give at least one product stream (P1) comprising unreacted hydroperoxide, unreacted organic compound and reacted organic compound,
    in the intermediate treatment (I1), base is added to the product stream or streams (P1) to give at least one product stream (PI1),
    in the reaction stage (R2), unreacted hydroperoxide and unreacted organic compound present in the product stream or streams (PI1) are reacted in at least two reactors connected in parallel to give at least one product stream (P2) comprising unreacted hydroperoxide,
    in an intermediate treatment (I2), unreacted hydroperoxide is separated by distillation from the product stream or streams (P2) to give at least one product stream (PI2) comprising hydroperoxide, and
    the hydroperoxide present in the product stream or streams (PI2) is reacted with organic compound in a reaction stage (R3) to give at least one product stream (P3).

9. A process as claimed in claim 1, wherein fixed-bed reactors are used as reactors.

10. A process as claimed in claim 1, wherein isothermal fixed-bed reactors are used.

11. A process as claimed in claim 1, wherein hydrogen peroxide is reacted with alkene to give alkene oxide using as catalyst a zeolite catalyst.

12. A process as claimed in claim 11, wherein hydrogen peroxide is reacted with propene, to give propylene oxide, using as catalyst a titanium silicalite catalyst having the TS-1 structure.

* * * * *